(12) United States Patent
Kuo et al.

(10) Patent No.: US 9,771,262 B1
(45) Date of Patent: Sep. 26, 2017

(54) METHOD FOR ORGANIC COMPOUND DEGRADATION AND METHOD FOR PRODUCING HYDROGEN

(71) Applicant: National Taiwan University of Science and Technology, Taipei (TW)

(72) Inventors: Dong-Hau Kuo, Taipei (TW); Xiaoyun Chen, Taipei (TW)

(73) Assignee: National Taiwan University of Science and Technology, Taipei (TW)

(*) Notice: Subject to any disclaimer, the term of this patent is extended or adjusted under 35 U.S.C. 154(b) by 0 days.

(21) Appl. No.: 15/476,674

(22) Filed: Mar. 31, 2017

Related U.S. Application Data

(63) Continuation-in-part of application No. 15/155,651, filed on May 16, 2016, now Pat. No. 9,649,622.

(51) Int. Cl.
    *C01B 3/26* (2006.01)
    *C01B 3/22* (2006.01)
    *B01J 27/043* (2006.01)
    *B01J 27/051* (2006.01)

(52) U.S. Cl.
    CPC ............ *C01B 3/22* (2013.01); *B01J 27/043* (2013.01); *B01J 27/051* (2013.01); *C01B 2203/1076* (2013.01)

(58) Field of Classification Search
    CPC ......... B01J 27/043; B01J 27/051; C01B 3/22; C01B 3/26; C01B 3/2203; C01B 3/1076; C01B 2203/1223; C01B 2203/1229; C01B 2203/1041; C01B 2203/1052; C01B 2203/1088; B01D 2255/20761; B01D 2255/20769; B01D 2255/20792; B01D 2255/2098
    USPC ............................... 502/216, 220; 423/648.1
See application file for complete search history.

(56) References Cited

U.S. PATENT DOCUMENTS

| | | | |
|---|---|---|---|
| 5,122,357 A | 6/1992 | Bedard et al. | |
| 5,594,263 A | 1/1997 | Bedard et al. | |
| 9,649,622 B1 * | 5/2017 | Kuo | ........................ B01J 27/02 |
| 2004/0029726 A1 | 2/2004 | Domen et al. | |

FOREIGN PATENT DOCUMENTS

WO      8706138      10/1987

* cited by examiner

*Primary Examiner* — Patricia L Hailey
(74) *Attorney, Agent, or Firm* — J.C. Patents

(57) ABSTRACT

A bimetal oxysulfide solid-solution catalyst is provided. The bimetal oxysulfide solid-solution catalyst is represented by the following formula:

$$Cu_xM^{(2)}_yO_zS_\gamma$$

wherein $M^{(2)}$ includes monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo), $0<y<0.3$, $0.7<x<1.0$, $0<z<0.5$, and $0.5<\gamma<1.0$. In addition, a manufacturing method of the bimetal oxysulfide solid-solution catalyst and applications of the bimetal oxysulfide solid-solution catalyst are also provided.

9 Claims, 5 Drawing Sheets

METHOD FOR ORGANIC COMPOUND DEGRADATION AND METHOD FOR PRODUCING HYDROGEN

CROSS-REFERENCE TO RELATED APPLICATION

This application is a continuation-in-part application of and claims the priority benefit of a prior application Ser. No. 15/155,651, filed on May 16, 2016, now U.S. Pat. No. 9,649,622. The entirety of the above-mentioned patent application is hereby incorporated by reference herein and made a part of this specification.

BACKGROUND OF THE INVENTION

1. Field of the Invention

The present invention generally relates to a catalyst, a manufacturing method of the catalyst, a method of carbon dioxide ($CO_2$) reduction using the catalyst, a method of heavy metal reduction using the catalyst, a method of hydrogenation of organic compounds, a method of organic compound degradation, and a method of hydrogen production. In particular, the present invention relates to an oxysulfide catalyst including copper.

2. Description of Related Art

Recently, global warming and climate change has become a huge threat to the environment. Therefore, $CO_2$ emission is an important issue awaiting to be solved worldwide. In particular, a method of converting $CO_2$ into ethanol ($C_2H_5OH$) using ruthenium (Ru) metal complex has been proposed. However, such mechanism requires external energy, such as external high power light sources, to trigger the reaction. Therefore, it is difficult to conduct the conversion at room temperature and atmosphere pressure. High power light sources not only impose a burden on the cost of the conversion, but also raise safety issues on a scale-up production system. Therefore, providing catalyst which enables elimination of $CO_2$ while being cost effective has become a topic to be researched in the field.

One of the heavy metal ions with highly toxic property is hexavalent chromium (Cr(VI)) which is widely used in industrial activities such as plastic, leather, textile, metal, electroplating processing, etc. The existence of Cr(VI) in drinking water has engrossed the attention of many scientists to remediate it due to its poisonous property and adverse effect on drinking water. The highly mobile nature and non biodegradability of Cr(VI) are not only harmful to aqueous environment but also to human life. Therefore, the reduction of Cr(VI) is highly required for environmental remediation.

Hydrogenation of organic compounds involves in many chemical reactions to facilitate the formation of second compound. The hydrogenation reaction has been popular to undergo with the hydrogen gas flow and catalyst of Pt, Pd, Ni, etc. High temperature is needed for the $H_2$-involving reaction. The reduction reaction at mild condition for a green and safe synthesis is encouraging.

SUMMARY OF THE INVENTION

The invention provides a catalyst and a manufacturing thereof, which effectively aids the conversion of $CO_2$ gas into ethanol, effectively aids the reduction of heavy metal, or effectively aids the hydrogenation of organic compounds at atmospheric condition.

The invention provides a bimetal oxysulfide solid-solution catalyst. The catalyst is represented by formula (1):

$$M^{(1)}_x M^{(2)}_y O_z S_\gamma \quad (1),$$

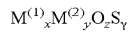

wherein in formula (1), $M^{(1)}$ includes a multivalent metal and $M^{(2)}$ includes a mono-, di-, tri-, tetra-, or penta-valent metal; $0<y<0.3$; $0.7<x<1.0$; $0<z<0.5$; $0.5<\gamma<1.0$.

In an embodiment of the invention, $M^{(1)}$ includes Copper (Cu) and the bimetal oxysulfide solid-solution catalyst is represented by formula (2):

$$Cu_x M^{(2)}_y O_z S_\gamma \quad (2),$$

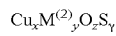

wherein in formula (2), $M^{(2)}$ comprises the mono-, di-, tri-, tetra-, or penta-valent metal; $0<y<0.3$; $0.7<x<1.0$; $0<z<0.5$; $0.5<\gamma<1.0$.

In an embodiment of the invention, in formula (2), $M^{(2)}$ includes monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo).

The invention provides a manufacturing method of the bimetal oxysulfide solid-solution catalyst. First, a copper-containing salt is dissolved in distilled water to obtain a first solution. Meanwhile, an $M^{(2)}$-containing compound is dissolved in distilled water to obtain a second solution. The first solution and the second solution are mixed to obtain a mixture solution. An organosulfur compound is added into the mixture solution, and the mixture solution is heated to a temperature range of 50-100° C. A precipitate is centrifuged from the mixture solution and is dried to obtain the bimetal oxysulfide solid-solution catalyst.

In an embodiment of the invention, the method further includes a step of adding hydrazine to the mixture solution in a dropwise manner.

The invention provides a method for $CO_2$ reduction. First, the bimetal oxysulfide solid-solution catalyst and a reactant solution are provided in the reactor. Subsequently, $CO_2$ gas is passed into the reactor to react with the reactant solution.

The invention provides a method for heavy metal reduction. First, the bimetal oxysulfide solid-solution catalyst is provided in a reactor. Then, a heavy metal aqueous solution is added to the reactor. Subsequently, the bimetal oxysulfide solid-solution catalyst and the heavy metal aqueous solution are reacted.

In an embodiment of the invention, the heavy metal includes hexavalent chromium (Cr(VI)).

The invention provides a method for the hydrogenation of organic compounds at an atmospheric condition. First, the bimetal oxysulfide solid-solution catalyst, an aqueous solution of organic compounds, and a reducing agent are added to a reactor. Subsequently, the bimetal oxysulfide solid-solution catalyst and the organic aqueous solution are reacted.

In an embodiment of the invention, the compounds includes rhodamine B, methyl orange, or methylene blue.

In an embodiment of the invention, the reducing agent includes sodium boron hydride or oxalic acid.

The invention provides a method for organic compound degradation. First, a bimetal oxysulfide solid-solution catalyst is provided. An aqueous solution of the organic compound and the bimetal oxysulfide solid-solution catalyst are added into a reactor. The bimetal oxysulfide solid-solution catalyst and the aqueous solution of the organic compound are reacted.

In an embodiment of the invention, the organic compound includes methylene blue.

In an embodiment of the invention, the bimetal oxysulfide solid-solution catalyst includes monovalent Silver (Ag), divalent Zinc (Zn), Manganese (Mn), Nickel (Ni), Cobalt (Co), and Tin (Sn$^{II}$), trivalent Indium (In), Cerium (Ce), Antimony (Sb), and Gallium (Ga), tetravalent Tin (Sn$^{IV}$), or pentavalent Molybdenum (Mo).

In an embodiment of the invention, the reactor is shielded from an ambient light.

The invention provides a method for producing hydrogen. First, a bimetal oxysulfide solid-solution catalyst dispersed in an aqueous solution is provided. Alcohol or organic acid is added into a catalytic reactor. After adding alcohol or organic acid into the catalytic reactor, the bimetal oxysulfide solid-solution catalyst starts to react.

In an embodiment of the invention, the alcohol includes methanol or ethanol.

In an embodiment of the invention, the organic acid includes acetic acid.

In an embodiment of the invention, the bimetal oxysulfide solid-solution catalyst includes monovalent Silver (Ag), divalent Zinc (Zn), Manganese (Mn), Nickel (Ni), Cobalt (Co), and Tin (Sn$^{II}$), trivalent Indium (In), Cerium (Ce), Antimony (Sb), and Gallium (Ga), tetravalent Tin (Sn$^{IV}$), or pentavalent Molybdenum (Mo).

In an embodiment of the invention, the catalytic reactor is shielded from an ambient light.

Based on the above, the bimetal oxysulfide solid-solution catalyst of the invention includes copper element and may be manufactured at a low temperature. Due to the specific structure of the catalyst of the invention, $CO_2$ gas may be converted to ethanol and reduction of heavy metal and the hydrogenation/degradation of organic chemicals may be performed at atmospheric condition. Moreover, hydrogen may also be produced under atmospheric condition with the aid of the bimetal oxysulfide solid-solution catalyst of the invention. As such, the power requirement for external energy may be eliminated. In addition, the bimetal oxysulfide solid-solution catalyst of the invention may be recycled. Therefore, the cost for the reduction processes may be significantly lowered.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1A:
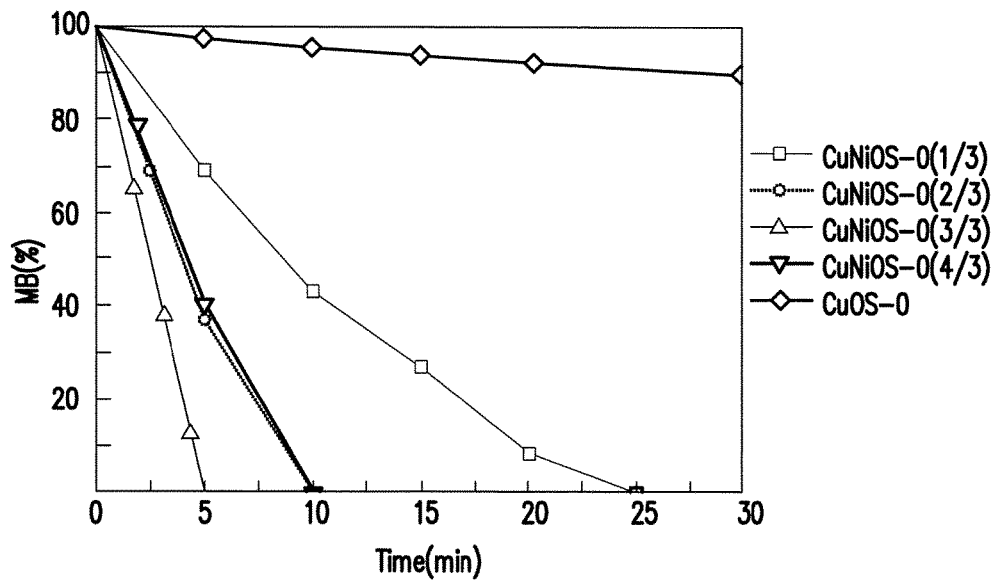
FIG. 1A is a diagram illustrating the ability of ethylene blue degradation in the dark for powders 13-17.

Reference will now be made in detail to the present preferred embodiments of the invention, examples of which are illustrated in the accompanying drawings. Wherever possible, the same reference numbers are used in the drawings and the description to refer to the same or like parts.

A bimetal oxysulfide solid-solution catalyst is prepared at a low temperature condition. Specifically, 4.6 grams of a $M^{(1)}$-containing salt is dissolved in distilled water to obtain a first solution. Meanwhile, 2 grams to 6 grams of an $M^{(2)}$-containing compound is dissolved in 250 mL of distilled water to obtain a second solution. $M^{(1)}$ is a multivalent metal. For example, $M^{(1)}$ may be copper and the $M^{(1)}$-containing salt may be copper nitrate. However, it construes no limitation in the invention. Other suitable copper-containing salt may be used as well. On the other hand, $M^{(2)}$ is, for example, mono-, di-, tri-, tetra-, or penta-valent metal. Specific examples of $M^{(2)}$ includes, but not limited to, monovalent Silver (Ag), divalent Zinc (Zn), Manganese (Mn), Nickel (Ni), Cobalt (Co), and Tin (Sn$^{II}$), trivalent Indium (In), Cerium (Ce), Antimony (Sb), and Gallium (Ga), tetravalent Tin (Sn$^{IV}$), pentavalent Molybdenum (Mo), or other similar metal elements. In other words, examples of the $M^{(2)}$-containing compound may include zinc acetate dihydrate, manganese (II) chloride, cobalt (II) chloride, nickel (II) chloride, indium (III) chloride, tin (II) chloride, cerium (III) nitrate hexahydrate, antimony (III) chloride, gallium (III) acetate, tin (IV) chloride hydrate, molybdenum (V) chloride, silver (I) nitrate, or other metal salts. However, they construe no limitation in the disclosure. Other compounds including suitable metal compounds may also be adapted. Subsequently, the first solution and the second solution are mixed while being stirred by a magnet for 30 minutes to obtain a mixture solution. An organosulfur compound having a concentration of 15 g/L is added into the mixture solution and the mixture solution is allowed to react with the organosulfur compound for 30 minutes. The organosulfur compound is, for example, thioacetamide or other suitable compound. Subsequently, the mixture solution is heated to a temperature range of 50° C. to 100° C. and 0.15 mL of hydrazine is added to the mixture solution in a dropwise manner to react for 2 hours. Thereafter, the precipitate is centrifuged. After rinsing the precipitate with distilled water until the precipitate is neutral, the precipitate is further rinsed twice with absolute ethanol. The precipitate is dried by an evaporator to obtain a bimetal oxysulfide solid-solution catalyst.

The bimetal oxysulfide solid-solution catalyst obtained is represented by formula (1):

$$M^{(1)}_x M^{(2)}_y O_z S_{1-z} \tag{1}$$

in formula (1), $M^{(1)}$ includes Copper (Cu) and $M^{(2)}$ includes monovalent Silver (Ag), divalent Zinc (Zn), Manganese (Mn), Nickel (Ni), Cobalt (Co), and Tin (Sn$^{II}$), trivalent Indium (In), Cerium (Ce), Antimony (Sb), and Gallium (Ga), tetravalent Tin (Sn$^{IV}$), or pentavalent Molybdenum (Mo), 0<y<0.3, 0.7<x<1.0, 0<z<0.5, and 0.5<γ<1.0.

The bimetal oxysulfide solid-solution catalyst obtained may have various applications. For example, the bimetal oxysulfide solid-solution catalyst may be used for $CO_2$ reduction, heavy metal reduction, or hydrogenation of organic compounds.

Specifically, when the bimetal oxysulfide solid-solution catalyst is used for $CO_2$ reduction, 0.1 gram of catalyst is provided in a reactor. Subsequently, 100 mL of reactant solution is added to the reactor. The reactant solution is, for example, a solution includes water. The reactant solution and the bimetal oxysulfide solid-solution catalyst are being stirred with a magnet with a stirring speed of 280 rpm (revolutions per minute). Thereafter, $CO_2$ gas is passed into the reactor to react with the reactant solution. In the present embodiment, the $CO_2$ gas may be generated by decomposing sodium bicarbonate ($NaHCO_3$) with the droplet addition of diluted nitric acid ($HNO_3$) aqueous solution to control the $CO_2$ generation. However, it construes no limitation in the invention. Other alternative $CO_2$ gas source may be adapted. The $CO_2$ gas is allowed to react with the reactant solution for 16-24 hours to generate ethanol. In other words, the bimetal oxysulfide solid-solution catalyst of the present embodiment aids the conversion of $CO_2$ gas into ethanol. It should be noted that the foregoing process is conducted at atmospheric condition. In other words, the process is performed at room temperature under atmosphere pressure. Alternatively speaking, only ambient light is present and no additional energy source is required. However, the invention is not limited thereto. In some other alternative embodiments, the reaction may be conducted in a dark room. That is, the reaction may be performed without the presence of any external energy.

In some alternative embodiments, the bimetal oxysulfide solid-solution catalyst of the invention may be used for heavy metal reduction. Specifically, when the bimetal oxysulfide solid-solution catalyst is used for heavy metal reduction, 0.1 grams of the bimetal oxysulfide solid-solution catalyst is provided in a reactor. Subsequently, 100 mL of a heavy metal aqueous solution with a concentration of 50 ppm is added into the reactor. The heavy metal is, for example, metallic element having an atomic number of 20 or greater. In the present embodiment, the heavy metal may include environment harmful hexavalent chromium (Cr (VI)). However, it construes no limitation in the invention. Other heavy metals may also be the subject for reduction. Thereafter, shake the reactor to render a uniform distribution of the bimetal oxysulfide solid-solution catalyst in the heavy metal aqueous solution. The bimetal oxysulfide solid-solution catalyst and the heavy metal aqueous solution are allowed to react for 2 minutes, so as to perform heavy metal reduction.

In some alternative embodiments, the bimetal oxysulfide solid-solution catalyst may be recycled. For example, after the foregoing heavy metal reduction process, the bimetal oxysulfide solid-solution catalyst may be centrifuged to separate from the solution. Without rinsing the bimetal oxysulfide solid-solution catalyst, the foregoing step of heavy metal reduction may be repeated again.

In some alternative embodiments, the bimetal oxysulfide solid-solution catalyst of the invention may be used for the hydrogenation of organic compounds. Specifically, when the bimetal oxysulfide solid-solution catalyst is used for hydrogenation reaction, 100 mL of aqueous solution of organic compounds (a dye aqueous solution) with a concentration of 100 ppm is add into in a 250 mL conical flask. Subsequently, 5 mL of reducing agent aqueous solution with a concentration of 0.1 mole is added into the conical flask. The organic compound is, for example, hydrocarbon having double or triple bonds. In the present embodiment, the organic compound may include methylene blue, methylene orange, or rhodamine B. However, it construes no limitation in the invention. Other organic compounds may also be the subject for hydrogenation reaction. On the other hand, the reducing agent is, for example, sodium boron hydride or oxalic acid. Under the stirring condition, 0.01 grams of the bimetal oxysulfide solid-solution catalyst is provided in the conical flask. Thereafter, shake the conical flask to render a uniform distribution of the bimetal oxysulfide solid-solution catalyst in the dye aqueous solution. The bimetal oxysulfide solid-solution catalyst and the dye aqueous solution are allowed to react for hydrogenation reaction.

In some alternative embodiments, the bimetal oxysulfide solid-solution catalyst of the invention may be used for degradation of organic compounds. Specifically, when the bimetal oxysulfide solid-solution catalyst is used for degradation, 100 mL of aqueous solution of organic compounds (a dye aqueous solution) and the bimetal oxysulfide solid-solution catalyst are added into a reactor for reaction. The organic compound is, for example, methylene blue. However, it construes no limitation in the invention. Other organic compounds may also be the subject for degradation. The degradation reaction may occur in a dark room condition. In other words, the reactor is shielded from an ambient light. The reactant mixture is under magnetic stirring with 280 r/m. 3 mL sample is taken every 5 minutes from the reactor. Thereafter, the degradation ratio of the organic compound is calculated.

In some alternative embodiments, the bimetal oxysulfide solid-solution catalyst of the invention may be used for producing hydrogen. Specifically, when the bimetal oxysulfide solid-solution catalyst is used for hydrogen production, alcohol or organic acid was added into a catalyst dispersion solution containing 225 mg of catalyst to from a total 450 mL batch solution. The alcohol is, for example, methanol or ethanol. On the other hand, the organic acid may be acetic acid. However, it construes no limitation in the invention. Other alcohols and organic acids may also be used for hydrogen production. The hydrogen production reaction may occur in a dark room condition. In other words, the reactor is shielded from an ambient light. The gas sampling is taken in the time interval of 20 minutes. A hydrogen calibration line may be built to quantitatively measure the $H_2$ generation rate.

The examples of the invention will be described in detail below.

Synthesis Example 1: Copper Zinc Oxysulfide ($Cu_xZn_yO_zS_y$) Powder 1

4.6 grams of copper nitrate ($Cu(NO_3)_2.2.5H_2O$) is dissolved in 250 mL of distilled water to obtain a first solution. 6.0 grams of zinc acetate dihydrate ($Zn(CH_3COO)_2.2H_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 1.

Synthesis Example 2: Copper Manganese Oxysulfide ($Cu_xMn_yO_zS_y$) Powder 2

4.6 grams of copper nitrate ($Cu(NO_3)_2.2.5H_2O$) is dissolved in 250 mL of distilled water to obtain a first solution.

2.0 grams of manganese (II) chloride ($MnCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 2.

Synthesis Example 3: Copper Cobalt Oxysulfide ($Cu_xCo_yO_zS_y$) Powder 3

4.6 grams of copper nitrate ($Cu(NO_3)_2 \cdot 2.5H_2O$) is dissolved in 250 mL of distilled water to obtain a first solution. 3.0 grams of cobalt (II) chloride ($CoCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 3.

Synthesis Example 4: Copper Nickel Oxysulfide ($Cu_xNi_yO_zS_y$) Powder 4

4.6 grams of copper nitrate ($Cu(NO_3)_2 \cdot 2.5H_2O$) is dissolved in 250 mL of distilled water to obtain a first solution. 3.0 grams of nickel (II) chloride ($NiCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 4.

Synthesis Example 5: Copper Indium Oxysulfide ($Cu_xIn_yO_zS_y$) Powder 5

4.6 grams of copper nitrate ($Cu(NO_3)_2 \cdot 2.5H_2O$) is dissolved in 250 mL of distilled water to obtain a first solution. 3.0 grams of indium (III) chloride ($InCl_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 5.

Synthesis Example 6: Copper Tin (II) Oxysulfide ($Cu_xSn^{II}_yO_zS_y$) Powder 6

4.6 grams of copper nitrate ($Cu(NO_3)_2 \cdot 2.5H_2O$) is dissolved in 250 mL of distilled water to obtain a first solution. 3.0 grams of anhydrous tin (II) chloride ($SnCl_2$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 6.

Synthesis Example 7: Copper Cerium Oxysulfide ($Cu_xCe_yO_zS_y$) Powder 7

4.6 grams of copper nitrate ($Cu(NO_3)_2 \cdot 2.5H_2O$) is dissolved in 250 mL of distilled water to obtain a first solution. 4.64 grams of cerium (III) nitrate hexahydrate ($Ce(NO_2)_3 \cdot 6H_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 85° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 7.

Synthesis Example 8: Copper Antimony Oxysulfide ($Cu_xSb_yO_zS_y$) Powder 8

4.6 grams of copper nitrate ($Cu(NO_3)_2 \cdot 2.5H_2O$) is dissolved in 250 mL of distilled water to obtain a first solution. 3.0 grams of antimony (III) chloride ($SbCl_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 8.

Synthesis Example 9: Copper Gallium Oxysulfide ($Cu_xGa_yO_zS_\gamma$) Powder 9

4.6 grams of copper nitrate ($Cu(NO_3)_2 \cdot 2.5H_2O$) is dissolved in 250 mL of distilled water to obtain a first solution. 3.0 grams of gallium (III) acetate ($Ga(CH_3COO)_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 95° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 9.

Synthesis Example 10: Copper Tin (IV) Oxysulfide ($Cu_xSn^{IV}{}_yO_zS_\gamma$) Powder 10

4.6 grams of copper nitrate ($Cu(NO_3)_2 \cdot 2.5H_2O$) is dissolved in 250 mL of distilled water to obtain a first solution. 4.0 grams of tin (IV) chloride hydrate ($SnCl_4 \cdot xH_2O$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 90° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 10.

Synthesis Example 11: Copper Molybdenum Oxysulfide ($Cu_xMo_yO_zS_\gamma$) Powder 11

4.6 grams of copper nitrate ($Cu(NO_3)_2 \cdot 2.5H_2O$) is dissolved in 250 mL of distilled water to obtain a first solution. 3.0 grams of molybdenum (V) chloride ($MoCl_5$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 95° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 11.

Synthesis Example 12: Copper Silver Oxysulfide ($Cu_xAg_yO_zS_\gamma$) Powder 12

4.6 grams of copper nitrate ($Cu(NO_3)_2 \cdot 2.5H_2O$) is dissolved in 250 mL of distilled water to obtain a first solution. 3.0 grams of silver (I) nitrate ($AgNO_3$) is dissolved in 250 mL of distilled water to obtain a second solution. The first solution and the second solution are mixed while being stirred by a magnet for 30 minutes to obtain a mixture solution. Thereafter, 100 mL of thioacetamide ($CH_3CSNH_2$) solution having a concentration of 15 g/L is added to the mixture solution and the mixture solution is allowed to react with the thioacetamide solution for 30 minutes. Subsequently, the mixture solution is heated to 80° C. and 0.15 mL of hydrazine is added to the mixture solution in a dropwise manner to react for 2 hours. The precipitate is centrifuged. After rinsing the precipitate with distilled water until the precipitate is neutral, the precipitate is further rinsed twice with absolute ethanol. The precipitate is dried by an evaporator to obtain powder 12.

CO$_2$ Reduction Reaction

Example 1: CO$_2$ Reduction Reaction for Ethanol Using Catalyst Powder 1

The catalytic reduction of $CO_2$ is conducted in a quartz glass reactor. 0.1 grams of the catalyst powder 1 and 100 mL of distilled water are added to the reactor and are being stirred with a magnet with a stirring speed of 280 rpm (revolutions per minute). Subsequently, $CO_2$ gas is passed into the reactor. The $CO_2$ gas is generated by decomposing sodium bicarbonate ($NaHCO_3$) with the addition of diluted nitric acid ($HNO_3$) aqueous solution (V:V) in a dropwise manner. The $CO_2$ gas is allowed to react with the distilled water for 16-24 or t hours, depending upon the rate of $NaHCO_3$ consumption. The volume $V_1$ (unit:mL) of excessive amount of the non-reacted $CO_2$ passed into the reactor is measured by collecting gas over water displacement method. In other words, the volume of non-reacted $CO_2$ in the reactor during the duration of the reaction time of t hours is denoted by $V_1$. After the reaction time of t hours, the remaining $NaHCO_3$ is continued to be decomposed by the addition of $HNO_3$, and the volume $V_2$ (unit:mL) of $CO_2$ gas generated herein is measured by collecting gas over water displacement method. Another trial of decomposing $NaHCO_3$ without the presence of the catalyst is performed, and the volume of $CO_2$ generated is denoted by $V_0$. Specifically, in the present embodiment, 5.0 grams of $NaHCO_3$ has been decomposed and 1295 mL of $CO_2$ is obtained. In other words, $V_0$ is a constant value of 1295 mL in the present embodiment.

The volume $V_3$ of $CO_2$ gas being converted with the aid of the catalyst may be calculated by the following formula:

$$V_3 = V_0 - V_1 - V_2.$$

The volume $V_3$ of $CO_2$ converting into ethanol can be calculated in terms of reaction rate with the unit of mmol/g·h by the following formula:

$$R(\text{mmol}/g \cdot h) = \frac{(V_3/1000)}{22.4 \times m \times t}$$

R is the ethanol generation rate, t is the reaction time (unit:hour), m is the amount of catalyst used (unit:g), and 22.4 L/mole is the molar volume of ideal gas at STP condition.

It should be noted that no other organic compounds except for ethanol is detected in the solution. Moreover, the procedure of Example 1 has been conducted thrice. The first trial and the second trial are conducted with the presence of ambient light. The third trial is conducted in a dark room. In other words, no external energy is present in the third trial. The amount of ethanol obtained in Example 1 is illustrated in Table 1 below.

Examples 2-8: $CO_2$ Reduction Reaction for Ethanol Using Catalyst Powders 2-8

Similar procedures as that of Example 1 have been conducted except the catalyst powder 1 is replaced by catalyst powders 2-8 respectively in Examples 2-8 and the procedures of some Examples have not been conducted for the second/third trials. It should be noted that Example 2-8 are only performed at a condition in which ambient light is present. The amount of ethanol obtained in Examples 2-8 are summarized in Table 1 below.

Example 9: $CO_2$ Reduction Reaction for Ethanol Using the Recycled Catalyst Powder 1 after the First Trial Similar procedure as that of Example 1 for powder 1 under the ambient light has been conducted for the recycled powder 1 after the first trial. The amount of ethanol obtained in Example 9 are summarized in Table 1 below.

Comparative Example 1: $CO_2$ Reduction Reaction for Ethanol Using Catalyst Powder Having a Chemical Formula of $CuO_zS_\gamma$ Similar procedure as that of Example 1 has been conducted except the catalyst powder 1 is replaced by catalyst powder having a chemical formula of $CuO_zS_\gamma$ without the second metal $M^{(2)}$ from its precursor. The amount of ethanol obtained in Comparative Example 1 is summarized in Table 1 below.

TABLE 1

| | Catalyst | $C_2H_5OH$ rate for first trial in ambient light (mmol/g · h) | $C_2H_5OH$ rate for second trial in ambient light (mmol/g · h) | $C_2H_5OH$ rate for third trial in dark room (mmol/g · h) | $C_2H_5OH$ rate for the used catalyst in ambient light (mmol/g · h) |
|---|---|---|---|---|---|
| Example 1 | $Cu_xZn_yO_zS_\gamma$ | 14.98 (12.79)* | 12.00 | 6.6 (6.5)* | — |
| Example 2 | $Cu_xMn_yO_zS_\gamma$ | 9.34 (9.45)* | 7.83 | — | — |
| Example 3 | $Cu_xCo_yO_zS_\gamma$ | 8.37 (8.39)* | 7.96 | — | — |
| Example 4 | $Cu_xNi_yO_zS_\gamma$ | 7.28 (7.13)* | 7.58 | — | — |
| Example 5 | $Cu_xIn_yO_zS_\gamma$ | 6.49 (6.64)* | 6.14 | — | — |
| Example 6 | $Cu_xSn^{II}_yO_zS_\gamma$ | 14.51 (14.66)* | 14.61 | — | — |
| Example 7 | $Cu_xCe_yO_zS_\gamma$ | 6.30 (6.24)* | — | — | — |
| Example 8 | $Cu_xSb_yO_zS_\gamma$ | 5.76 (5.90)* | — | — | — |
| Example 9 | $Cu_xZn_yO_zS_\gamma$ | — | — | — | 11.48 |
| Comparative Example 1 | $CuO_zS_\gamma$ | 0 | — | — | — |

*The values in brackets are the ethanol generation rate obtained by GC-FID.

The numerical value of ethanol obtained in Table 1 is the amount of ethanol obtained per hour per gram of catalyst powder used. As clearly illustrated in Table 1, the bimetal oxysulfide solid-solution catalyst of the invention is able to aid the conversion of $CO_2$ gas to ethanol under atmospheric condition or in a dark room. As such, the power requirement for external energy may be eliminated. In addition, as the reduction duration lasting for 16-24 hours, the second trials with the new catalyst has the similar ethanol generation rate to the first one. Moreover, as clearly illustrated in Example 9, the ethanol generation rate obtained by recycling used bimetal oxysulfide solid-solution catalyst is still decent, thereby proving the reusability of the bimetal oxysulfide solid-solution catalyst of the invention. Therefore, the cost of the reduction process may be significantly lowered.

In order to verify the volume $V_3$ of $CO_2$ gas is converted to ethanol, the following verification procedure is performed on the mixture solution.

Verification Method: Gas Chromatography-Flame Ionization Detector (GC-FID)

A GC-FID detector is being used to measure the ethanol concentration in the mixture solution for the ethanol generation rate. The testing condition is as follows:

HP-INNDWAX capillary column: 30 m×0.25 mm
Device: FID detector
Inlet temperature: 200° C.
Split ratio: 100:1
Sample volume: 2 μL
Column oven temperature: 180° C.
Detector temperature: 200° C.
Flow rate of hydrogen gas: 35 mL/min
Flow rate of air: 400 mL/min
Flow rate of high purity $N_2$ assist gas: 30 mL/min The ethanol generation rates were confirmed by GC-FID detector for Examples 1-8 in the ambient light and for Example 1 in the dark room. The data were shown in the brackets in Table 1 and matches with the results obtained from the $CO_2$ volume conversion.

Based on the verification method above, it is apparent that the bimetal oxysulfide solid-solution catalyst of the invention is able to aid the conversion of $CO_2$ to ethanol. In other words, by using the bimetal oxysulfide solid-solution catalyst of the invention, undesired $CO_2$ gas can be easily converted to useful fuel sources without the presence of external energy. Therefore, the reduction of $CO_2$ gas may be achieved at a lower cost.

Heavy Metal Reduction Reaction

Example 1: Hexavalent Chromium (Cr(VI)) Reduction Reaction Using Catalyst Powder 1

0.1 grams of the catalyst powder 1 is placed in a 250 mL conical flask. Subsequently, 100 mL of hexavalent chromium (Cr(VI)) aqueous solution with a concentration of 50 ppm is added into the conical flask. Thereafter, shake the conical flask to render a uniform distribution of the catalyst powder 1 in the hexavalent chromium aqueous solution. The catalyst powder 1 and the hexavalent chromium aqueous solution are allowed to react for 2 minutes. Subsequently, a sample of 2 mL of the solution is filter by a syringe filter. The absorbance of the sample is measured by UV-VIS spectrophotometer and the concentration of the hexavalent chromium in the sample is calculated according to Lambert-Beer Law.

The foregoing process may be repeated with the catalyst powder 1 being recycled. In detail, the catalyst powder 1 may be centrifuged to separate from the solution. Without rinsing the catalyst powder 1, the foregoing process is repeated for 6 times.

The removal rate of hexavalent chromium in the solution is illustrated in Table 2 below. It should be noted that the removal rate of the hexavalent chromium may be calculated by comparing the original hexavalent chromium concentration and the remaining hexavalent chromium concentration after the heavy metal reduction reaction.

Examples 2-7: Hexavalent Chromium (Cr(VI)) Reduction Reaction Using Catalyst Powders 2-6, 11

Similar procedure as that of Example 1 has been conducted except the catalyst powder 1 is replaced by catalyst powders 2-6 respectively in Examples 2-6, and by catalyst powder 11 in Example 7. The removal rates of hexavalent chromium in the solution are summarized in Table 2 below.

TABLE 2

| | Catalyst | First Trial (%) | Second Trial (%) | Third Trial (%) | Fourth Trial (%) | Fifth Trial (%) | Sixth Trial (%) |
|---|---|---|---|---|---|---|---|
| Example 1 | $Cu_xZn_yO_zS_\gamma$ | 100 | 100 | 100 | 97.8 | 94.1 | 82.9 |
| Example 2 | $Cu_xMn_yO_zS_\gamma$ | 100 | 100 | 100 | 100 | 97.2 | 94.6 |
| Example 3 | $Cu_xCo_yO_zS_\gamma$ | 100 | 100 | 100 | 100 | 97.2 | 93.8 |
| Example 4 | $Cu_xNi_yO_zS_\gamma$ | 100 | 100 | 100 | 97.7 | 96.9 | 95.0 |
| Example 5 | $Cu_xIn_yO_zS_\gamma$ | 100 | 100 | 97.6 | 96.0 | 93.3 | 90.5 |
| Example 6 | $Cu_xSn^{II}_yO_zS_\gamma$ | 100 | 100 | 96.9 | 95.1 | 94.1 | 84.4 |
| Example 7 | $Cu_xMo_yO_zS_\gamma$ | 100 | 99.3 | 98.7 | 95.6 | 91.1 | — |

Examples 8-12: Hexavalent Chromium (Cr(VI)) Reduction Reaction Using Catalyst Powders 7-10 and 12

Similar procedure as that of Example 1 has been conducted except the catalyst powder 1 is replaced by catalyst powders 7-10 respectively in Examples 8-11, and by catalyst powder 12 in Example 12 and the hexavalent chromium aqueous solutions are allowed to react for 60 minutes. The removal rates of hexavalent chromium in the solution are 18% for Example 8 ($Cu_xCe_yO_zS_\gamma$), 38.5% for Example 9 ($Cu_xSb_yO_zS_\gamma$), 32.2% for Example 10 ($Cu_xGa_yO_zS_\gamma$), 85.7% for Example 11 ($Cu_xSn^{IV}_yO_zS_\gamma$), and 5.3% for Example 12 ($Cu_xAg_yO_zS_\gamma$).

It is commonly known that hexavalent chromium is highly toxic. As clearly illustrated in Table 2, the catalyst of the invention is able to aid the elimination of hexavalent chromium under atmospheric condition in a fast rate. 0.1 g of the catalyst is able to remove 0.03 g Cr(VI) in a short period and is still available. The resulting solution may be recycled for other use without causing damage to human body. In addition, as illustrated in Table 2, when the catalyst is recycled, the ability of aiding the conversion is not compromised. Therefore, the cost for the reduction processes may be significantly lowered.

Hydrogenation Reaction of Organic Compounds

Example 1 (RhB): Rhodamine B Hydrogenation Reaction Using Catalyst Powder 1

50 mL of Rhodamine B aqueous solution (a dye solution) with a concentration of 20 ppm is add into a 100 mL conical flask. Subsequently, 5 mL of sodium boron hydride aqueous solution with a concentration of 0.1 mole is added into the conical flask. Under the stirring condition, 0.01 grams of catalyst powder 1 is provided in the conical flask. The catalyst powder 1 and the Rhodamine B aqueous solution are allowed to react. Subsequently, a sample of 2 mL of the solution is taken out after the dye colour change into colourless and filter by a syringe filter. The absorbance of the filtered solution is measured by UV-VIS spectrophotometer and the dye concentration in the sample is calculated according to Lambert-Beer Law.

The time required for the complete hydrogenation reaction of Rhodamine B in the solution is illustrated in Table 3 below. It should be noted that the complete reduction of the Rhodamine B may be calculated by comparing the original Rhodamine B concentration without the addition of sodium boron hydride and the remaining dye concentration after the hydrogenation reduction reaction.

Examples 2-12 (RhB): Rhodamine B Hydrogenation Reactions Using Catalyst Powders 2-12

Similar procedure as that of Example 1 (RhB) has been conducted except the catalyst powder 1 is replaced by catalyst powders 2-12 respectively in Examples 2-12 (RhB). The times required for the complete hydrogenation reaction of Rhodamine B in the solution are summarized in Table 3 below.

Examples 1-12 (MO): Methyl Orange Hydrogenation Reactions Using Catalyst Powders 1-12

Similar procedure as that of Example 1 (RhB) has been conducted for catalyst powders 1-12 respectively in Examples 1-12 (MO) except for Rhodamine B changed to methyl orange. The times required for the complete hydrogenation reaction of methyl orange in the solution are summarized in Table 3 below.

Examples 1-12 (MB): Methylene Blue Hydrogenation Reactions Using Catalyst Powders 1-12

Similar procedure as that of Example 1 (RhB) has been conducted for catalyst powders 1-12 respectively in Examples 1-12 (MB) except for Rhodamine B changed to methylene blue and its dye solution changed to 100 mL of methylene blue aqueous solution with a concentration of 100 ppm in a 250 mL conical flask. The times required for the complete hydrogenation reaction of methylene blue in the solution are summarized in Table 3 below.

Comparative Example 1 (RhB): Rhodamine B Hydrogenation Reactions Using Catalyst $CuO_zS_\gamma$ Similar procedure as that of Example 1 (RhB) has been conducted. The times required for the complete hydrogenation reaction of Rhodamine B in the solution are summarized in Table 3 below.

Comparative Example 1 (MO): Methyl Orange Hydrogenation Reactions Using Catalyst $CuO_zS_\gamma$ Similar procedure as that of Example 1 (MO) has been conducted. The times required for the complete hydrogenation reaction of methyl orange in the solution are summarized in Table 3 below.

Comparative Example 1 (MB): Methylene Blue Hydrogenation Reactions Using Catalyst $CuO_zS_\gamma$ Similar procedure as that of Example 1 (MB) has been conducted. The times required for the complete hydrogenation reaction of methylene blue in the solution are summarized in Table 3 below.

condition involve the green chemical processes, which can be beneficial for the industry, biology, and pharmacy.

Organic Compound Degradation

Synthesis Example 13: Copper Nickel Oxysulfide ($Cu_xNi_yO_zS_\gamma$) Powder 13

Under magnetic stirring, 1.5 grams of thioacetamide ($CH_3CSNH_2$) is added into a 500 ml solution containing cupric nitrate ($Cu(NO_3)_2.2.5H_2O$) and nickel (II) chloride ($NiCl_2.6H_2O$) with the molar ratio of n(Ni):n(Cu)=1/3. After 30 minutes of stirring, the mixture solution is heated to 95° C. with a heating rate of 2° C./min. The mixture solution is further stirred for 2 hours. The precipitate solid is collected by centrifugation and is washed with deionized water until pH=7. The precipitate solid is further washed with absolute ethanol for two times. Finally, the solid is vacuum dried at 80° C. for 24 hours. The obtained powder 13 is labelled as CuNiOS-0 (1/3).

Synthesis Examples 14-16: Copper Nickel Oxysulfide ($Cu_xNi_yO_zS_\gamma$) Powders 14-16

Similar procedures as that of Synthesis Example 13 is conducted except the cupric nitrate ($Cu(NO_3)_2.2.5H_2O$) and nickel (II) chloride ($NiCl_2.6H_2O$) molar ratio (n(Ni):n(Cu)) are substituted with 2/3, 3/3, 4/3. The obtained powders 14-16 are respectively labelled as CuNiOS-0 (2/3), CuNiOS-0 (3/3), CuNiOS-0 (4/3).

Synthesis Example 17: Copper Oxysulfide (CuOS) Powder 17

For comparison, the Ni-free CuOS powder 17 is synthesized with the same procedure as that of Synthesis Example 13 except for the elimination of Ni precursor.

Synthesis Examples 18-21: Copper Nickel Oxysulfide ($Cu_xNi_yO_zS_\gamma$) Powders 18-21

Similar procedures as that of Synthesis Example 15 is conducted except 0.1, 0.2, 0.3, or 0.4 mL of hydrazine

TABLE 3

| | Catalyst | Time for completing hydrogenation of Rhodamine B (RhB) (minute) | Time for completing hydrogenation of Methyl orange (MO) (minute) | Time for completing hydrogenation of Methylene blue (MB) (minute) |
|---|---|---|---|---|
| Example 1 | $Cu_xZn_yO_zS_\gamma$ | 1 | slow | 3 |
| Example 2 | $Cu_xMn_yO_zS_\gamma$ | 2 | 3 | 5 |
| Example 3 | $Cu_xCo_yO_zS_\gamma$ | 2 | 1 | 3 |
| Example 4 | $Cu_xNi_yO_zS_\gamma$ | 1 | 1 | 4 |
| Example 5 | $Cu_xIn_yO_zS_\gamma$ | 2 | slow | 4 |
| Example 6 | $Cu_xSn^{II}_yO_zS_\gamma$ | 1 | 2 | 3 |
| Example 7 | $Cu_xCe_yO_zS_\gamma$ | 2 | slow | 2 |
| Example 8 | $Cu_xSb_yO_zS_\gamma$ | slow | 4 | 6 |
| Example 9 | $Cu_xGa_yO_zS_\gamma$ | 2 | slow | 8 |
| Example 10 | $Cu_xSn^{IV}_yO_zS_\gamma$ | 2 | slow | 13 |
| Example 11 | $Cu_xMo_yO_zS_\gamma$ | slow | 1 | 3 |
| Example 12 | $CuAg_yO_zS_\gamma$ | No reaction | No reaction | No reaction |
| Comparative Example 1 | $CuO_zS_\gamma$ | 2 | 3 | 3 |

The hydrogenation reactions of rhodamine B, methyl orange, and methylene blue under catalyst involve the C—N=C bonding in molecules changed to C—NH—C. $Cu_xSn^{II}_yO_zS_\gamma$ performs the best in all three different organic molecules. These hydrogenation reactions at the ambient ($N_2H_4$) is added to the mixture solution after the mixture solution was heated to 95° C. The obtained powders 18-21 are respectively labelled as CuNiOS-1, CuNiOS-2, CuNiOS-3, and CuNiOS-4.

The manufacturing parameters of powders 13-21 are summarized in Table 4 below.

TABLE 4

| Powder Number | Labelling | Ni/Cu precursor weight ratio | Amount of hydrazine added (mL) |
|---|---|---|---|
| 13 | CuNiOS-0 (1/3) | 1/3 | 0 |
| 14 | CuNiOS-0 (2/3) | 2/3 | 0 |
| 15 | CuNiOS-0 (3/3) | 3/3 | 0 |
| 16 | CuNiOS-0 (4/3) | 4/3 | 0 |
| 17 | CuOS-0 | N/A | 0 |
| 18 | CuNiOS-1 | 3/3 | 0.1 |
| 19 | CuNiOS-2 | 3/3 | 0.2 |
| 20 | CuNiOS-3 | 3/3 | 0.3 |
| 21 | CuNiOS-4 | 3/3 | 0.4 |

Synthesis Example 22: Copper Cobalt Oxysulfide ($Cu_xCo_yO_zS_y$) Powder 22

Under magnetic stirring, 1.5 grams of thioacetamide ($CH_3CSNH_2$) is added into a 500 ml solution containing cupric nitrate ($Cu(NO_3)_2 \cdot 2.5H_2O$) and cobalt (II) chloride ($CoCl_2$) with the molar ratio of n(Co):n(Cu)=3/3. After 30 minutes of stirring, the mixture solution is heated to 95° C. with a heating rate of 2° C./min. The mixture solution is further stirred for 2 hours. The precipitate solid is collected by centrifugation and is washed with deionized water until pH=7. The precipitate solid is further washed with absolute ethanol for two times. Finally, the solid is vacuum dried at 80° C. for 24 hours. The obtained powder 22 is labelled as CuCoOS-0.

Synthesis Examples 23-29: Copper Cobalt Oxysulfide ($Cu_xCo_yO_zS_y$) Powders 23-29

Similar procedures as that of Synthesis Example 22 is conducted except 0.1 or 0.3 mL of hydrazine ($N_2H_4$) is added to the mixture solution after the mixture solution was heated to 95° C. The obtained powders 23-24 are respectively labelled as CuCoOS—N1 and CuCoOS—N2. Similar procedures as that of Synthesis Example 22 is conducted except 0.25, 0.5, 0.75, 1.0, or 2.0 mL of hydrogen peroxide ($H_2O2$) is added to the mixture solution after the mixture solution was heated to 95° C. The obtained powders 25-29 are respectively labelled as CuCoOS—O1, CuCoOS—O2, CuCoOS—O3, CuCoOS—O4, and CuCoOS—O5.

Synthesis Example 30: Copper Indium Oxysulfide ($Cu_xIn_yO_zS_y$) Powder 30

Under magnetic stirring, 1.5 grams of thioacetamide ($CH_3CSNH_2$) is added into a 500 ml solution containing cupric nitrate ($Cu(NO_3)_2 \cdot 2.5H_2O$) and indium (III) chloride ($InCl_3$) with the molar ratio of n(In):n(Cu)=3/3. After 30 minutes of stirring, the mixture solution is heated to 95° C. with a heating rate of 2° C./min. The mixture solution is further stirred for 2 hours. The precipitate solid is collected by centrifugation and is washed with deionized water until pH=7. The precipitate solid is further washed with absolute ethanol for two times. Finally, the solid is vacuum dried at 80° C. for 24 hours. The obtained powder 30 is labelled as CuInOS-0.

Synthesis Example 31: Copper Indium Oxysulfide ($Cu_xIn_yO_zS_y$) Powder 31

Similar procedures as that of Synthesis Example 30 is conducted except 0.5 mL of hydrogen peroxide ($H_2O_2$) is added to the mixture solution after the mixture solution was heated to 95° C. The obtained powder 31 labelled as CuInOS-0.5$H_2O_2$.

The manufacturing parameters of powders 22-31 are summarized in Table 5 below.

TABLE 5

| Powder Number | Labelling | Amount of hydrazine added (mL) | Amount of hydrogen peroxide added (mL) |
|---|---|---|---|
| 22 | CuCoOS-0 | 0 | 0 |
| 23 | CuCoOS—N1 | 0.1 | 0 |
| 24 | CuCoOS—N2 | 0.3 | 0 |
| 25 | CuCoOS—O1 | 0 | 0.25 |
| 26 | CuCoOS—O2 | 0 | 0.50 |
| 27 | CuCoOS—O3 | 0 | 0.75 |
| 28 | CuCoOS—O4 | 0 | 1.0 |
| 29 | CuCoOS—O5 | 0 | 2.0 |
| 30 | CuInOS-0 | 0 | 0 |
| 31 | CuInOS—0.5$H_2O_2$ | 0 | 0.5 |

Methylene Blue (MB) Degradation Measurements

CuNiOS catalytic degradation activity on methylene blue (MB) is tested in a home-made and jacketed quartz reactor. The reactor is shielded from an ambient light such that the catalytic reactions is conducted in a dark condition. For example, the reactor may be wrapped by an aluminium foil in order to avoid additional interference in interpreting the dye degradation mechanism. The catalytic degradation is tested with 100 mL MB solution of 10 mg/L while the catalyst concentration is kept at 0.25 g/L. The reactant mixture is under magnetic stirring with 280 r/min. A sample of 3 mL is taken every 5 minutes from the reactor, followed by instant centrifugation in 1 minute. Absorbance of the supernatant is measured with JASCD V-670 UV-Vis spectrophotometer at 663 nm. The concentration of the samples is calculated based on the Lambert-Beer law. The degradation ratio of MB is calculated using the following expression:

$$\text{Degradation ratio of MB} = (C_0 - C_t)/C_0 \times 100\%,$$

where $C_0$ is the initial concentration at t=0 minute and $C_t$ is the concentration after reaction for t minutes. To evaluate the reusability of CuNiOS, the catalysts after the first run without being washed is reused for the next trial at the same condition after re-filling with a fresh MB dye solution.

The experimental results are demonstrated in FIG. 1A to FIG. 1D.

FIG. 1A illustrated the ability of MB degradation in the dark for powders 13-17. It should be noted that the degradation activity of CuNiOS (powders 13-16) is much higher than CuOS (powder 17). Powder 15 (CuNiOS-0 (3/3)) is able to completely degrade MB in 5 minutes. On the contrary, powder 17 (CuOS-0) only removed 9.9% MB in 30 minutes. The degradation of MB with the efficiency is in the following order: Powder 15 (CuNiOS-0 (3/3))>Powder 14 (CuNiOS-0 (2/3)) Powder 16 (CuNiOS-0 (4/3))>Powder 13 (CuNiOS-0 (1/3))>Powder 17 (CuOS-0).

Figure 1B:
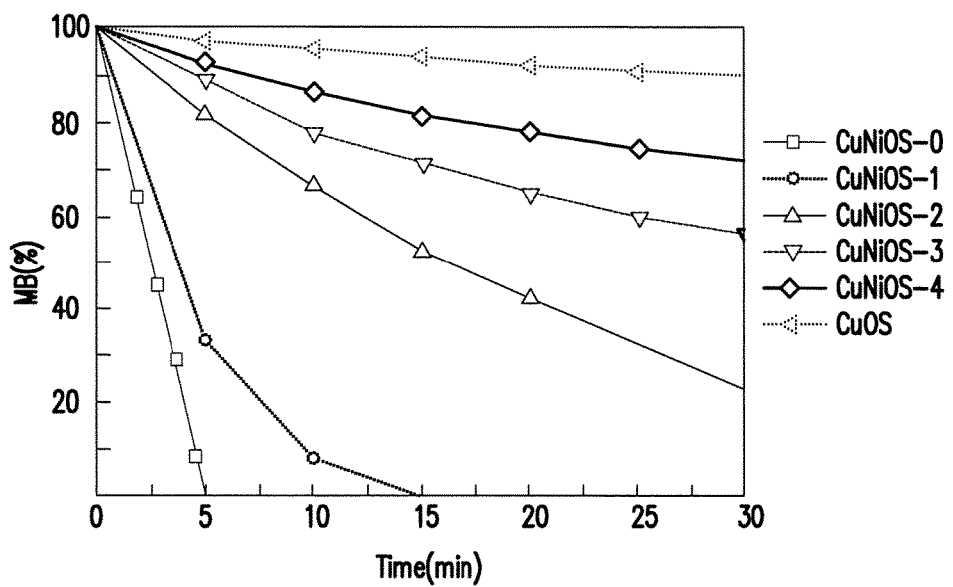
FIG. 1B is a diagram illustrating the ability of methylene blue degradation in the dark for powders 13, 17, 18-21.

FIG. 1B illustrated the ability of MB degradation in the dark for powders 13, 17, 18-21. As demonstrated in FIG. 1B, the hydrazine ($N_2H_4$) added during the synthesis step of the bimetal oxysulfide solid-solution catalyst has an important effect on the degradation of MB. The efficiency is in the following order: Powder 13 (CuNiOS-0)>Powder 18 (CuNiOS-1)>Powder 19 (CuNiOS-2)>Powder 20 (CuNiOS-3)>Powder 21 (CuNiOS-4)>Powder 17 (CuOS- 0). $N_2H_4$-free CuNiOS-0 is able to completely degrade MB in 5 minutes. On the contrary, the CuNiOS-4 catalyst (Powder 21) only removed 28.3% MB in 30 minutes. The data indicate that the addition of $N_2H_4$ for preparing CuNiOS has degraded its oxidation capability.

peroxide, the degradation of MB may be enhanced. The efficiency is in the following order: Powder 31 (CuInOS-0.5$H_2O_2$)>Powder 30 (CuInOS-0)>Powder 17 (CuOS-0).

The comparison of MB degradation with various catalysts is summarized in Table 6 below.

TABLE 6

| | | | Testing condition | | | | |
|---|---|---|---|---|---|---|---|
| Catalyst | Total Catalyst (mg) | MB solution (ppm) | total solution (ml) | Reaction time (min) | Light type | MB/Catal. (mg/mg) | Removal (%) |
| CuS + $H_2O_2$ | 10 mg | 10 ppm | 10 ml | 15 min | dark | 0.01 | 100 |
| Ag—In—Ni—S | 20 mg | 3.16 ppm | 14 ml | 12 min | dark | 0.002212 | 98 |
| NiS | 5 mg | 3.16 ppm | 14 ml | 15 min | dark | 0.008848 | 100 |
| $MoS_2$ + Ultrasonic wave | N/A | 10 ppm | N/A | 5 min | dark | N/A | 100 |
| $CeGeO_4$ | 150 mg | 6 ppm | 100 ml | 24 h | dark | 0.004 | 100 |
| ZnO:Eu | 100 mg | 10 ppm | 100 ml | 150 min | Xe-lamp 300 W | 0.01 | 88 |
| Ag/$Ag_3PO_4$ | 50 mg | 20 ppm | 50 ml | 120 min | Xe-lamp 500 W | 0.02 | 100 |
| Au/$SiO_2$/$WO_3$ | 10 mg | 4.9 ppm | 50 ml | 60 min | Xe-lamp 72 W | 0.0245 | 100 |
| $Mn_3O_4$—$MnO_2$ | 50 mg | 10 ppm | 100 ml | 60 min | Xe-lamp 300 W | 0.02 | 93.5 |
| $TiO_2$—GO | 20 mg | ~5 ppm | 50 ml | 25 min | UV-light 100 W | 0.0125 | 100 |
| CuNiOS-0 (Powder 13) | 25 mg | 10 ppm | 100 ml | 5 min | Dark | 0.04 | 100 |

In order to test the catalyst reusability, the supernatant of the best CuNiOS-0 catalyst for MB degradation after the first test is decanted. Then, a fresh 100 mL MB solution of 10 ppm is added for the reuse tests in the dark. The second run is also completed in 5 minutes. After the third run, the CuNiOS-0 remained effective to degrade 93% MB in 5 minutes. To differentiate the dye degradation from adsorption, the wash-out ethanol solution of CuNiOS-0 powder after the runs is analyzed with UV-Vis spectrophotometer at 663 nm. The disappearance of the characteristic peak confirmed there is no MB residues adsorbed on CuNiOS. A comparative experiment on activated carbon (AC) with $S_{BET}$ above 1000 $m^2$/g did show the characteristic peak at 663 nm for MB on AC after the activated carbon (AC) powder was washed. The bimetal oxysulfide solid-solution catalyst of the invention has a $S_{BET}$ value of ~22 $m^2 \cdot g^{-1}$, which is too low for adsorption to proceed. Therefore, the MB dye is confirmed to be degraded by the catalytic reaction in the dark.

Figure 1C:
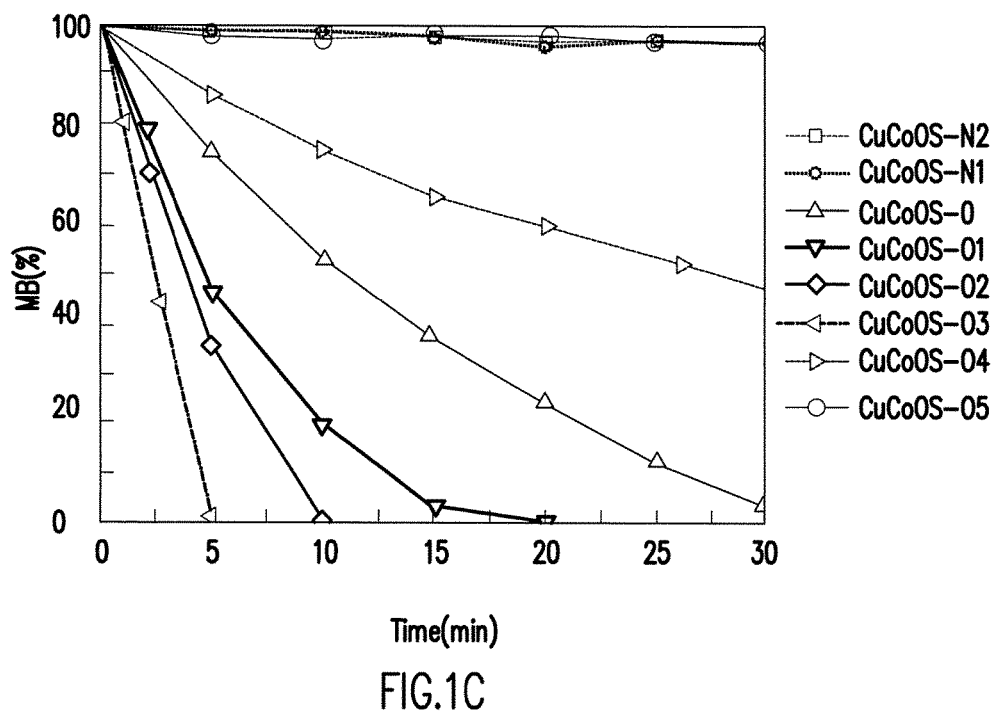
FIG. 1C is a diagram illustrating the ability of methylene blue degradation in the dark for powders 22-29.

FIG. 1C is a diagram illustrating the ability of methylene blue degradation in the dark for powders 22-29. As demonstrated in FIG. 1C, the hydrazine ($N_2H_4$) and the hydrogen peroxide ($H_2O_2$) added during the synthesis step of the bimetal oxysulfide solid-solution catalyst have an important effect on the degradation of MB. By adding sufficient amount of hydrogen peroxide, the degradation of MB is enhanced. However, adding too much hydrogen peroxide slows down the degradation of MB. The efficiency is in the following order: Powder 27 (CuCoOS—O3)>Powder 26 (CuCoOS—O2)>Powder 25 (CuCoOS—O1)>Powder 22 (CuCoOS-0)>Powder 28 (CuCoOS—O4)>Powder 29 (CuCoOS—O5)≈Powder 24 (CuCoOS—N2) Powder 23 (CuCoOS—N1).

Figure 1D:
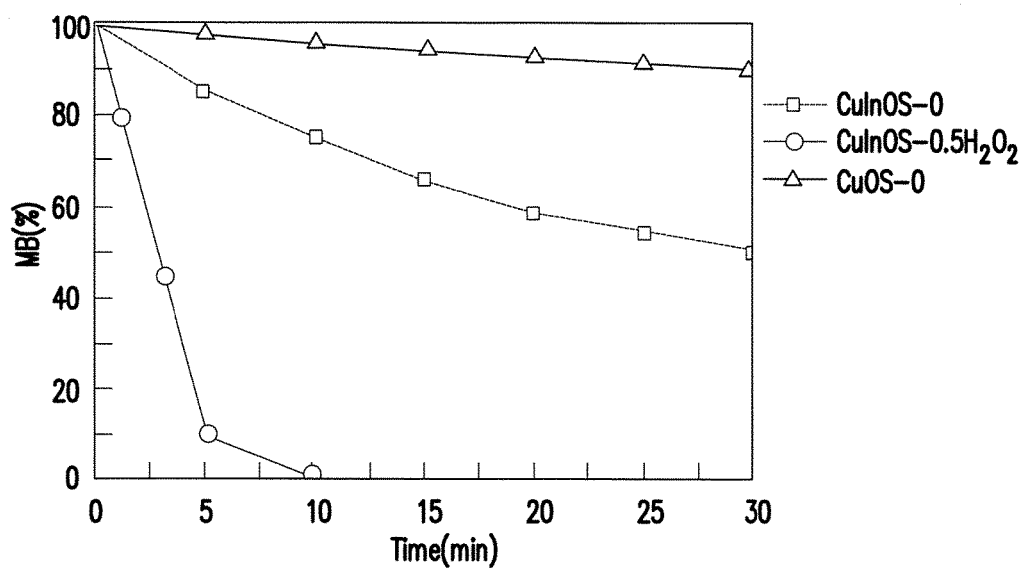
FIG. 1D is a diagram illustrating the ability of methylene blue degradation in the dark for powders 17, 30-31.

FIG. 1D is a diagram illustrating the ability of methylene blue degradation in the dark for powders 17, 30-31. As demonstrated in FIG. 1D, the hydrogen peroxide ($H_2O_2$) added during the synthesis step of the bimetal oxysulfide solid-solution catalyst has an important effect on the degradation of MB. By adding sufficient amount of hydrogen As seen in Table 6, with the bimetal oxysulfide solid-solution catalyst of the invention, the MB degradation takes the shortest time period. Moreover, no extra external energy is required when using the bimetal oxysulfide solid-solution catalyst of the invention.

Hydrogen Generation

Synthesis Example 32: Copper Cobalt Oxysulfide ($Cu_xCo_yO_zS_y$) Powder 32

Under magnetic stirring, 1.5 grams of thioacetamide ($CH_3CSNH_2$) is added into a 500 ml solution containing cupric nitrate ($Cu(NO_3)_2 \cdot 2.5H_2O$) and precursor (cobalt (II) chloride ($CoCl_2$)) with the molar ratio of n(Co):n(Cu)=1:1. After 30 minutes of stirring, the mixture solution is heated to 95° C. with a heating rate of 2° C./min. The mixture solution is further stirred for 2 hours. The precipitate solid is washed, dried, and collected. The obtained powder 32 is labelled as CuCoOs-0.

Synthesis Examples 33-36: Copper Nickel Oxysulfide ($Cu_xNi_yO_zS_y$) Powder 33, Copper Indium Oxysulfide ($Cu_xIn_yO_zS_y$) Powder 34, Copper Cerium Oxysulfide ($Cu_xCe_yO_zS_y$) Powder 35, and Copper Zinc Oxysulfide ($Cu_xZn_yO_zS_y$) Powder 36

Similar procedures as that of Synthesis Example 32 is conducted except the precursor is replaced by nickel (II) chloride ($NiCl_2 \cdot 6H_2O$), indium (III) chloride ($InCl_3 \cdot 4H_2O$), cerium (III) nitrate hexahydrate ($Ce(NO_2)_3 \cdot 6H_2O$), and zinc (II) acetate dihydrate ($Zn(CH_3COO)_2 \cdot 2H_2O$). The obtained powders 33-36 are respectively labelled as CuNiOS-0, CuInOS-0, CuCeOS-0, and CuZnOS-0.

Synthesis Example 37: Copper Oxysulfide (CuOS) Powder 37

For comparison, the CuOS powder 37 is synthesized with the same procedure as that of Synthesis Example 32 except for the elimination of precursor.

Synthesis Examples 38-41: Copper Cobalt Oxysulfide ($Cu_xCo_yO_zS_y$) Powders 38-41

Similar procedures as that of Synthesis Example 32 is conducted except 0.1, 0.2, 0.3, or 0.4 mL of hydrazine ($N_2H_4$) is added to the mixture solution after the mixture solution was heated to 95° C. The obtained powders 38-41 are respectively labelled as CuCoOS-1, CuCoOS-2, CuCoOS-3, and CuCoOS-4.

Synthesis Examples 42-47: Copper Manganese Oxysulfide ($Cu_xMn_yO_zS_y$) Powders 42-47

Similar procedures as that of Synthesis Example 32 is conducted except the precursor is replaced by manganese (II) chloride ($MnCl_2$). Moreover, 0, 0.1, 0.2, 0.3, or 0.4 mL of hydrazine ($N_2H_4$) is added to the mixture solution after the mixture solution was heated to 95° C. The obtained powders 42-46 are respectively labelled as CuMnOS-0, CuMnOS-1, CuMnOS-2, CuMnOS-3, and CuMnOS-4. Powder 42 further undergoes an annealing process at 200° C. and is labelled as CuMnOS-0-200 or Powder 47.

The manufacturing parameters of powders 32-47 are summarized in Table 7 below.

TABLE 7

| Powder Number | Labelling | Precursor | Amount of hydrazine added (mL) |
|---|---|---|---|
| 32 | CuCoOS-0 | Cobalt | 0 |
| 33 | CuNiOS-0 | Nickel | 0 |
| 34 | CuInOS-0 | Indium | 0 |
| 35 | CuCeOS-0 | Cerium | 0 |
| 36 | CuZnOS-0 | Zinc | 0 |
| 37 | CuOS | N/A | 0 |
| 38 | CuCoOS-1 | Cobalt | 0.1 |
| 39 | CuCoOS-2 | Cobalt | 0.2 |
| 40 | CuCoOS-3 | Cobalt | 0.3 |
| 41 | CuCoOS-4 | Cobalt | 0.4 |
| 42 | CuMnOS-0 | Manganese | 0 |
| 43 | CuMnOS-1 | Manganese | 0.1 |
| 44 | CuMnOS-2 | Manganese | 0.2 |
| 45 | CuMnOS-3 | Manganese | 0.3 |
| 46 | CuMnOS-4 | Manganese | 0.4 |
| 47 | CuMnOS-0-200 | Manganese | 0 |

Catalytic Hydrogen Generation

Hydrogen generation is conducted in a home-made and jacketed quartz reactor equipped with the input and output valves to control the gas flow. The reactor is shielded from an ambient light such that the catalytic reactions is conducted in a dark condition. In other words, to exclude the UV and visible light irradiations for the purpose of understanding the intrinsic nature for $H_2$ generation, the reactor may be wrapped by an aluminium foil. The input valve is connected to a gas tank of 99.99% Argon (Ar) and the output valve is connected to a well-callibrated gas chromatography (GC) with thermal conduction detector (TCD) system. The hydrogen generation reaction is carried out by well dispersing 225 mg of catalyst in an aqueous solution to react with methanol ($CH_3OH$), ethanol ($C_2H_5OH$), or acetic acid in a 450 ml reactor. The gas sampling is taken in the time interval of 20 min. Gas sampling is conducted by flowing the Ar gas through the reactor to GC-TCD system for several minutes. A hydrogen calibration line may be built to quantitatively measure the $H_2$ generation rate.

The experimental results are demonstrated in FIG. 2A to FIG. 2D, FIG. 3A to FIG. 3B, and Table 8.

Figure 2A:
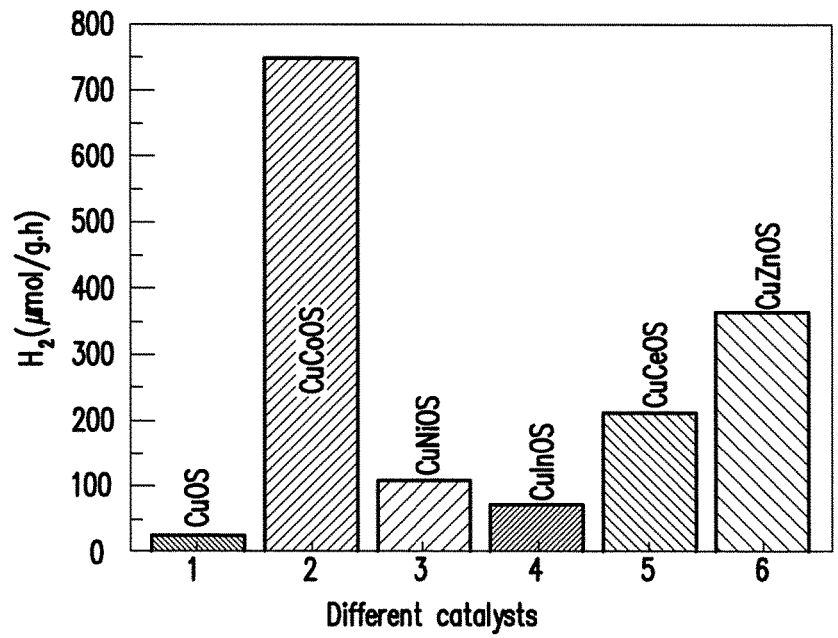
FIG. 2A is a diagram illustrating the ability of hydrogen production in the dark for powders 32-37.

FIG. 2A illustrated the hydrogen production rate in dark condition for powders 32-37. It should be noted that the aqueous solution for this set of experiment is by adding methanol into $H_2O$ to form 10% methanol solution. The hydrogen production efficiency is in the following order: Powder 32 (CuCoOS-0)>Powder 36 (CuZnOS-0)>Powder 35 (CuCeOS-0)>Powder 33 (CuNiOS-0)>Powder 34 (CuInOS-0)>Powder 37 (CuOS). Powder 32 (CuCoOS-0) has the highest hydrogen production rate at 748 $\mu mol \cdot g^{-1} \cdot h^{-1}$, while the hydrogen production rate is 27 $\mu mol \cdot g^{-1} \cdot h^{-1}$ for Powder 37 (CuOS). For comparative purpose, the trial using Pt-coated P25-$TiO_2$ as the catalyst (instead of the bimetal oxysulfide solid-solution catalyst of the invention) is also performed. However, Pt/P25-$TiO_2$ under the same condition did not have any hydrogen generation in the dark. The trial using Pt-coated P25-$TiO_2$ as the catalyst yields a $H_2$ generation rate of 129.3 $\mu mol \cdot g^{-1} \cdot h^{-1}$ under 350 W Xe lamp. Using the bimetal oxysulfide solid-solution catalyst of the invention as the catalyst indeed yields a higher hydrogen generation rate. Moreover, it is also confirmed that $H_2$ production from the liquid fuel at natural environment does happen with the aid of the bimetal oxysulfide solid-solution catalyst of the invention.

Figure 2B:
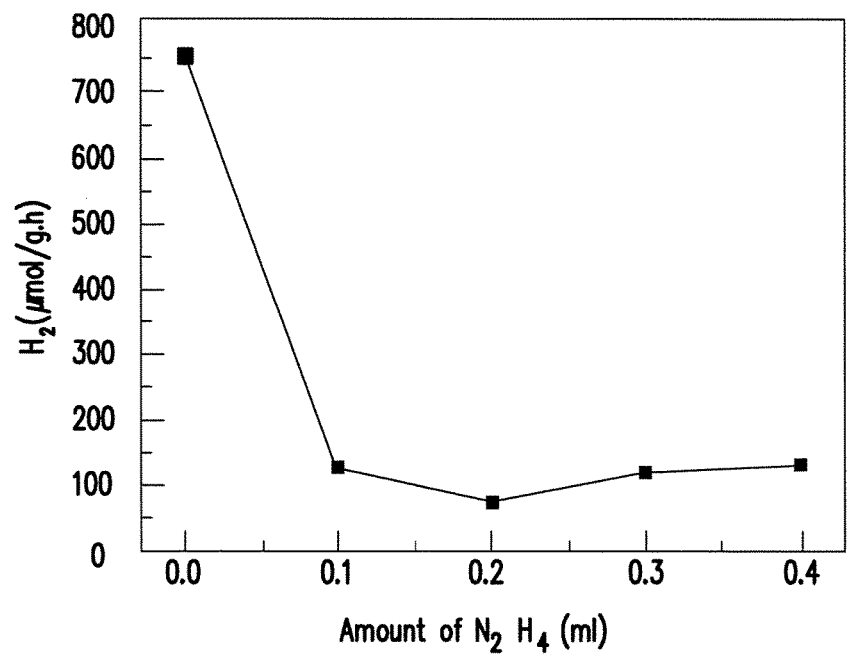
FIG. 2B is a diagram illustrating the ability of hydrogen production in the dark for powders 32, 38-41.

FIG. 2B illustrated the hydrogen production in dark condition for powders 32, 38-41. As demonstrated in FIG. 1B, the hydrazine ($N_2H_4$) added during the synthesis step of the bimetal oxysulfide solid-solution catalyst has an important effect on the hydrogen production rate. There is a trend of lowering the $H_2$ yield for CuCoOS prepared with a higher $N_2H_4$ amount, where CuCoOS shows a higher $S^{6+}/S^{2-}$ or $Cu^+/Cu^{2+}$ content. The Powder 32 (CuCoOS-0) without adding $N_2H_4$ had the highest $H_2$ yield.

Figure 2C:
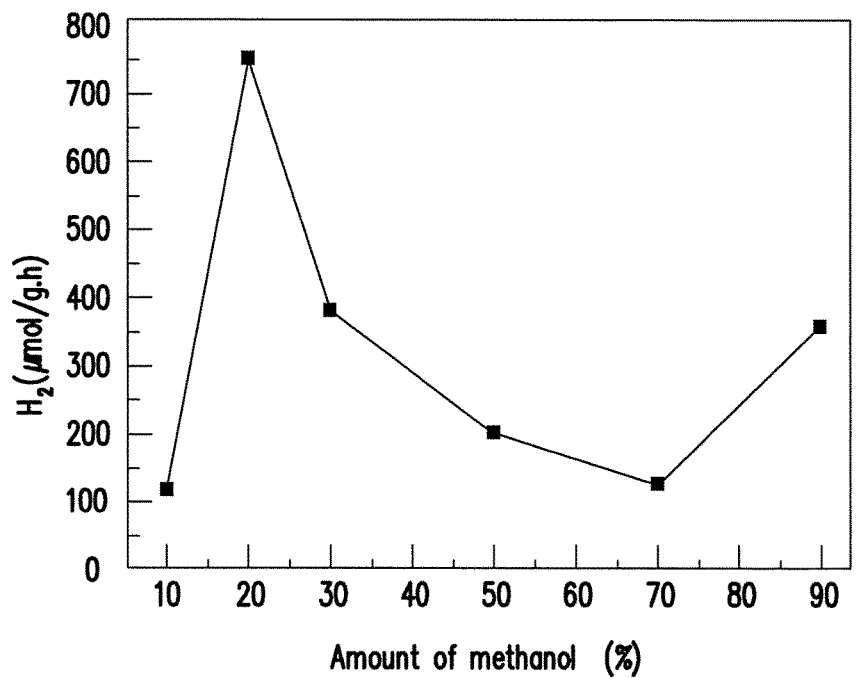
FIG. 2C is a diagram illustrating the hydrogen production in the solutions with different amount of methanol using powder 32.

FIG. 2C illustrated the $H_2$ production in the solutions with different amount of methanol using powder 32. It should be noted that the catalysts in pure $H_2O$ and methanol did not generate hydrogen, but the aqueous solutions of methanol produced $H_2$ at normal temperature and pressure (NTP) in the dark. Referring to FIG. 2A and FIG. 2C simultaneously, the highest $H_2$ yield of 748 $\mu mol \cdot g^{-1} \cdot h^{-1}$ in the 20% methanol solution (FIG. 2C) is much higher than that of CuOS at 27 $\mu mol \cdot g^{-1} \cdot h^{-1}$ (FIG. 2A). Moreover, the $H_2$ generation also occurred for Powder 32 (CuCoOS-0) in ethanol (231 $\mu mol \cdot g^{-1} \cdot h^{-1}$) solution and acetic acid (459 $\mu mol \cdot g^{-1} \cdot h^{-1}$) solution. For pure ethanol, pure acetic acid, and acid mixture solution of alcohol and acetic acid without water, no $H_2$ generation is observed. These results indicated that hydrogen generation process involves the reactions of catalysts with water and alcohol, or water and acetic acid. The reaction between catalyst and water, therefore, becomes critical.

Figure 2D:
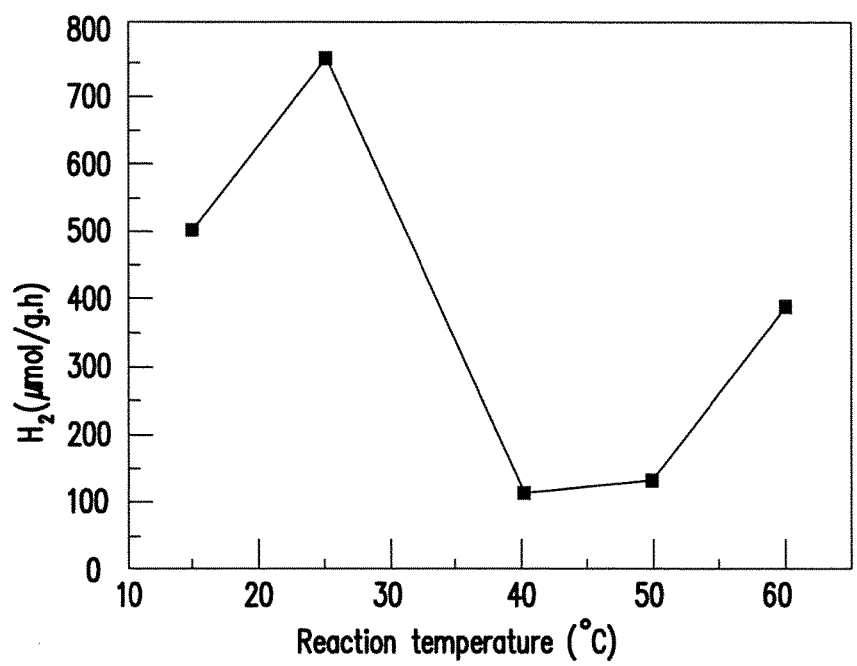
FIG. 2D is a diagram illustrating the hydrogen production at different reaction temperatures using powder 32.

FIG. 2D illustrated the $H_2$ production at different reaction temperatures range from 15° C. to 60° C. using powder 32. As illustrated in FIG. 2D, powder 32 (CuCoOS-0) showed the highest $H_2$ yield of 748 $\mu mol \cdot g^{-1} \cdot h^{-1}$ at 25° C. and became lower at higher temperatures. The increased yield at 60° C. and the decreased yield at 15° C. may be related to the thermal activation of other kinetic steps. As the major reaction at 25-50° C. (around room temperature) is not a thermal activation process, the occurrence of hydrogen generation involves a totally different reaction mechanism.

TABLE 8

| | | Condition | | | | |
|---|---|---|---|---|---|---|
| Catalyst | Dark/Light | 20% methanol + $H_2O$ | 20% ethanol + $H_2O$ | 20% ethanoic acid + $H_2O$ | $H_2O$ | ethanol |
| CuOS | Dark | 27 | 23 | — | 0 | 0 |
| CuMnOS-0 | Dark | 154 | 854 | 217 | 0 | 0 |
| CuMnOS-1 | Dark | 765 | 945 | — | 0 | 0 |
| CuMnOS-2 | Dark | 105 | 213 | — | — | — |
| CuMnOS-3 | Dark | 224 | 203 | — | — | — |
| CuMnOS-4 | Dark | 165 | 226 | — | — | — |
| CuMnOS-0 | Visible | 204 | 245 | — | — | — |
| CuMnOS-0-200 | Dark | 120 | — | — | — | — |

Note: Unit for the yield: $\mu mol \cdot g^{-1}$ catal. $\cdot h^{-1}$

As seen from Table 8, the highest $H_2$ yield is 765 $\mu mol \cdot g^{-1}$ catal. $\cdot h^{-1}$ in the methanol solution and 945 $\mu mol \cdot g^{-1}$ catal. $\cdot h^{-1}$ in the ethanol solution. These yields are higher than the trial using Powder 37 (CuOS) at 27 $\mu mol \cdot g^{-1}$ catal. $\cdot h^{-1}$. The $H_2$ generation also occurred for powder 42 (CuMnOS-0) with the yield of 217 $\mu mol \cdot g^{-1}$ catal. $\cdot h^{-1}$ in an ethanoic acid solution. Under the visible illumination of 150 W Halogen lamp, the $H_2$ yield degraded to 204 $\mu mol \cdot g^{-1}$ catal. $\cdot h^{-1}$ in methanol solution. The ineffectiveness of photo-induced electron-hole pairs under light illumination for $H_2$ production at NTP indicates dehydrogenation of $CH_3OH$ by aqueous CuMnOS-0 dispersion solution is not initiated by the electron/hole charges. After CuMnOS-0 nanoflower catalyst is annealed at 200° C. (Powder 47), its $H_2$ yield further degraded to 120 $\mu mol \cdot g^{-1}$ catal. $\cdot h^{-1}$ due to the deactivation of the catalyst activity. There is a trend of lowering the $H_2$ yield at the higher $Cu^+$ content for preparing CuMnOS with higher $N_2H_4$ amount. To test catalyst reusability, after immersing the CuMnOS-1 catalyst in alcohol solution for 24 hours, the step of drying and re-filling is performed and the catalyst is tested again. A $H_2$ yield of 663 $\mu mol \cdot g^{-1}$ catal. $\cdot h^{-1}$ is obtained.

For the photocatalytic reactions in the water/methanol solution, conventional $Ni_2P$/CdS nanorods obtained a record-high $H_2$ production rate of 553 $mmol \cdot g^{-1}$ catal. $\cdot h^{-1}$ under a filtered 300 W Xe lamp. The rate per input light power can be viewed as 1.84 $mmol \cdot g^{-1} \cdot catal. \cdot h^{-1} \cdot watt^{-1}$. The other excellent catalyst was Sr—$NaTaO_3$ with a rate of 48.9 $mmol \cdot g^{-1}$ catal. $\cdot h^{-1}$ or 0.79 $mmol \cdot g^{-1}$ catal. $\cdot h^{-1} \cdot watt^{-1}$. Ruthenium hydride complex performed the best for the homogeneous catalysis of methanol and water into $CO_2$ and $H_2O$ at 90° C. under the additive of KOH. Without the precious metal, the $H_2$ production rate is low. However, in the invention, the powder 43 (CuMnOS-1) may achieve a hydrogen generation rate of 945 $\mu mol \cdot g^{-1}$ catal. $\cdot h^{-1}$ even in the dark.

Reusability of the Bimetal Oxysulfide Solid-Solution Catalyst

Figure 3A:
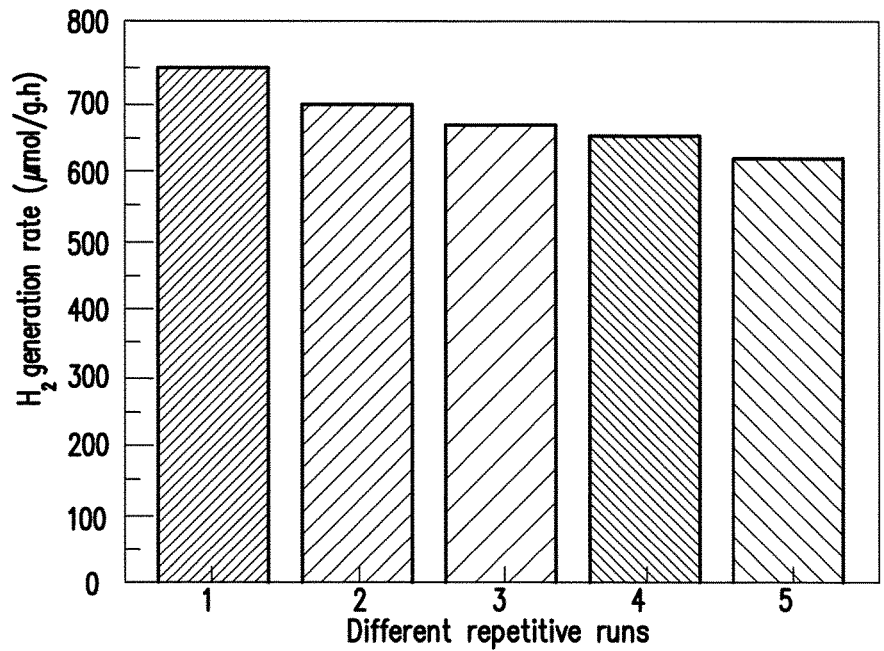
FIG. 3A is a diagram illustrating the reusability of powder 32 for hydrogen production.

FIG. 3A illustrated the reusability of Powder 32 (CuCoOS-0) for hydrogen production. The same powder had been used for 5 trials. After the 5th run, the CuCoOS-0 catalyst still maintained the hydrogen generation activity at 621 $\mu mol \cdot g-1 \cdot h-1$. There is a 17.0% decrease in the $H_2$ production rate after the 5th run, so the catalyst did slightly degrade for each reusability test. If the degradation involved the reactivity of CuCoOS, it is expected that the $Cu^+$ and $Cu^{2+}$ in CuCoOS should have a change from their original values of 66.5% and 33.5%, respectively, due to the redox reactions. Therefore, the CuCoOS catalyst after 5 runs needs to be evaluated for its Cu valence state.

Figure 3B:
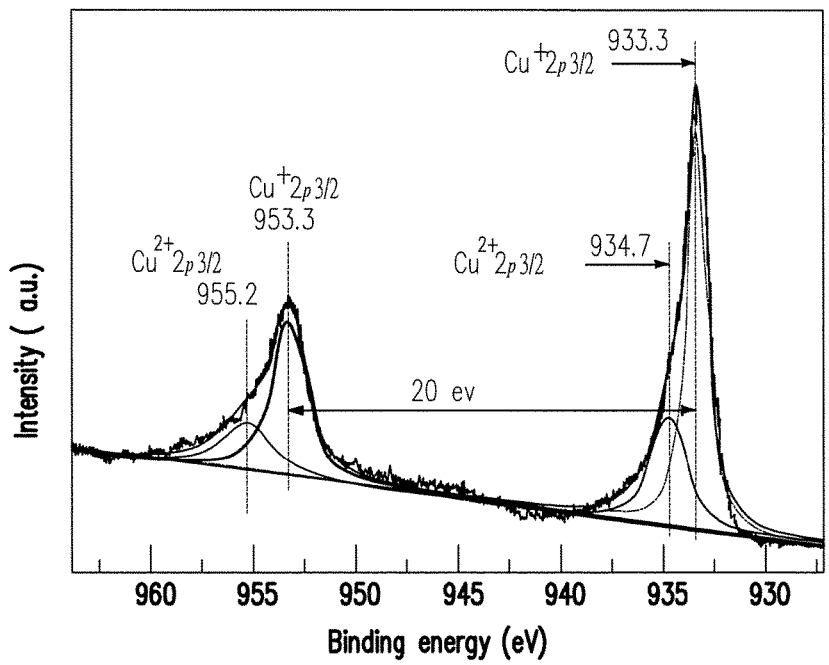
FIG. 3B is a diagram illustrating the high resolution Cu2p XPS spectrum of powder 32 after 5 runs.

FIG. 3B illustrated the high resolution Cu2p XPS spectrum of Powder 32 (CuCoOS-0) after 5 runs. The monovalent $Cu^+$ peaks of Cu2p3/2 and Cu2p1/2 located at 933.3 eV and 953.3 eV, respectively. The bivalent $Cu^{2+}$ peaks of 2p3/2 and 2p1/2 located at 934.7 eV and 955.2 eV, respectively. According to the peak area, the molar contents of $Cu^+$ and $Cu^{2+}$ are calculated to be 66.7% and 33.2%, respectively. It can been found that the XPS Cu2p peak positions and the $Cu^+$ and $Cu^{2+}$ contents are similar to those of the fresh CuCoOS-0 catalyst. The results indicated that the CuCoOS catalyst used 5 runs for the hydrogen generation is stable.

Based on the foregoing, the bimetal oxysulfide solid-solution catalyst in the invention includes several advantages. For example, the bimetal oxysulfide solid-solution catalyst may be manufactured at a low temperature, thereby ensure safety in the manufacturing process. Moreover, due to the specific structure and composition of the bimetal oxysulfide solid-solution catalyst of the invention, reduction of $CO_2$ gas, reduction of heavy metal, hydrogenation/degradation (oxidation) of organic compounds, and production of hydrogen may be performed at atmospheric condition. That is to say, the bimetal oxysulfide catalysts can be adjusted for the different redox reactions. As such, the power requirement for external energy may be eliminated. In addition, the bimetal oxysulfide solid-solution catalyst of the invention may be recycled for repeated uses. Therefore, the cost for the reduction/oxidation processes may be significantly lowered.

It will be apparent to those skilled in the art that various modifications and variations can be made to the structure and composition of the present invention without departing from the scope or spirit of the invention. In view of the foregoing, it is intended that the present invention covers modifications and variations of this invention provided they fall within the scope of the following claims and their equivalents.

What is claimed is:

1. A method for organic compound degradation, comprising:
   providing a bimetal oxysulfide solid-solution catalyst, wherein the bimetal oxysulfide solid-solution catalyst is represented by the following formula:

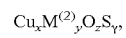
   $Cu_xM^{(2)}_yO_zS_\gamma$, $M^{(2)}$ comprises a mono-, di-, tri-, tetra-, or penta-valent metal; $0.7<x<1.0$; $0<y<0.3$; $0<z<0.5$; $0.5<\gamma<1.0$;
   adding an aqueous solution of the organic compound and the bimetal oxysulfide solid-solution catalyst into a reactor; and
   reacting the bimetal oxysulfide solid-solution catalyst and the aqueous solution of the organic compound.

2. The method for organic compound degradation according to claim 1, wherein the organic compound comprises methylene blue.

3. The method for organic compound degradation according to claim 1, wherein $M^{(2)}$ comprises monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo).

4. The method for organic compound degradation according to claim 1, wherein the reactor is shielded from an ambient light.

5. A method for producing hydrogen, comprising:
providing a bimetal oxysulfide solid-solution catalyst, wherein the bimetal oxysulfide solid-solution catalyst is represented by the following formula:

$$Cu_xM^{(2)}_yO_zS_\gamma,$$

$M^{(2)}$ comprises a mono-, di-, tri-, tetra-, or penta-valent metal; $0.7<x<1.0$; $0<y<0.3$; $0<z<0.5$; $0.5<\gamma<1.0$;
dispersing the bimetal oxysulfide solid-solution catalyst in an aqueous solution and adding the aqueous solution into a catalytic reactor;
adding alcohol or organic acid into the catalytic reactor;
reacting the bimetal oxysulfide solid-solution catalyst and the aqueous solution.

6. The method for producing hydrogen according to claim 5, wherein the alcohol comprises methanol or ethanol.

7. The method for producing hydrogen according to claim 5, wherein the organic acid comprises acetic acid.

8. The method for producing hydrogen according to claim 5, wherein $M^{(2)}$ comprises monovalent Silver (Ag), divalent Zinc (Zn), Manganese (Mn), Nickel (Ni), Cobalt (Co), and Tin ($Sn^{II}$), trivalent Indium (In), Cerium (Ce), Antimony (Sb), and Gallium (Ga), tetravalent Tin ($Sn^{IV}$), or pentavalent Molybdenum (Mo).

9. The method for producing hydrogen according to claim 5, wherein the catalytic reactor is shielded from an ambient light.

* * * * *